US010272035B2

(12) United States Patent
Peyman

(10) Patent No.: US 10,272,035 B2
(45) Date of Patent: *Apr. 30, 2019

(54) OPHTHALMIC DRUG DELIVERY METHOD

(71) Applicant: Gholam A. Peyman, Sun City, AZ (US)

(72) Inventor: Gholam A. Peyman, Sun City, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/269,444

(22) Filed: Sep. 19, 2016

(65) Prior Publication Data
US 2017/0000730 A1 Jan. 5, 2017

Related U.S. Application Data

(60) Continuation-in-part of application No. 13/457,568, filed on Apr. 27, 2012, now Pat. No. 9,486,357, which is a division of application No. 12/985,758, filed on Jan. 6, 2011, now abandoned, which is a continuation-in-part of application No. 12/611,682, filed on Nov. 3, 2009, now abandoned.

(60) Provisional application No. 61/114,143, filed on Nov. 13, 2008.

(51) Int. Cl.
| A61K 9/00 | (2006.01) |
| A61K 35/545 | (2015.01) |
| A61K 35/28 | (2015.01) |
| A61K 35/30 | (2015.01) |
| A61K 31/551 | (2006.01) |
| A61K 31/4439 | (2006.01) |
| A61K 31/4409 | (2006.01) |
| A61K 38/13 | (2006.01) |
| A61F 9/00 | (2006.01) |
| A61K 31/436 | (2006.01) |
| A61K 31/365 | (2006.01) |
| C12N 15/00 | (2006.01) |

(52) U.S. Cl.
CPC .......... A61K 9/0051 (2013.01); A61F 9/0017 (2013.01); A61K 9/0048 (2013.01); A61K 31/365 (2013.01); A61K 31/436 (2013.01); A61K 31/4409 (2013.01); A61K 31/4439 (2013.01); A61K 31/551 (2013.01); A61K 35/28 (2013.01); A61K 35/30 (2013.01); A61K 35/545 (2013.01); A61K 38/13 (2013.01); C12N 15/00 (2013.01)

(58) Field of Classification Search
CPC .................................................. A61K 9/0051
See application file for complete search history.

(56) References Cited

U.S. PATENT DOCUMENTS

| 4,781,675 | A | 11/1988 | White |
| 5,178,604 | A | 1/1993 | Baerveldt et al. |
| 5,366,501 | A | 11/1994 | Langerman |
| 5,370,607 | A | 12/1994 | Memmen |
| 5,454,796 | A | 10/1995 | Krupin |
| 5,628,795 | A | 5/1997 | Langerman |
| 5,725,493 | A | 3/1998 | Avery et al. |
| 5,830,173 | A | 11/1998 | Avery et al. |
| 6,096,076 | A | 8/2000 | Silvestrini |
| 6,117,675 | A | 9/2000 | van der Kooy et al. |
| 6,649,625 | B2 | 11/2003 | Azuma et al. |
| 6,673,812 | B1* | 1/2004 | Azuma ................. A61K 31/00 514/303 |
| 7,090,888 | B2 | 8/2006 | Snyder et al. |
| 7,276,050 | B2 | 10/2007 | Franklin |
| 7,278,990 | B2 | 10/2007 | Gwon |
| 7,767,803 | B2* | 8/2010 | Diener ................. A61K 31/787 435/6.14 |
| 7,794,437 | B2 | 9/2010 | Humayun et al. |
| 7,824,704 | B2 | 11/2010 | Anderson et al. |
| 8,663,194 | B2* | 3/2014 | Ambati ................. A61F 9/0017 604/289 |
| 9,486,357 | B2* | 11/2016 | Peyman ................. A61F 9/0017 |
| 2002/0071855 | A1 | 6/2002 | Sadozai et al. |
| 2003/0149873 | A1 | 8/2003 | Snyder et al. |
| 2003/0175324 | A1 | 9/2003 | Robinson et al. |
| 2004/0132725 | A1 | 7/2004 | Levitzki et al. |
| 2004/0137059 | A1 | 7/2004 | Nivaggioli et al. |
| 2005/0064010 | A1 | 3/2005 | Cooper et al. |
| 2006/0106455 | A1 | 5/2006 | Furst et al. |
| 2007/0031472 | A1 | 2/2007 | Huang et al. |
| 2007/0093892 | A1 | 4/2007 | Mackool |
| 2008/0058704 | A1* | 3/2008 | Hee ....................... A61F 9/0017 604/21 |
| 2009/0155338 | A1 | 6/2009 | Conway et al. |
| 2010/0119519 | A1 | 5/2010 | Peyman |
| 2011/0268807 | A1* | 11/2011 | Su ........................ A61K 9/0048 424/491 |

OTHER PUBLICATIONS

Yasukawa et al. Adv Drug Delivery Rev 2005;57:2033-46.*
Nagaoka et al. IOVS May 2008;49:2053-60.*
Bourges et al. Adv Drug Delivery Rew 2006;58:1182-1202.*
Hinderling et al. J Clin Pharm 2007;47:19-25.*
Li et al. Int J Radiation Oncol Biol. Phys. 2004;58:1215-27.*
Kita et al. PNAS Nov. 11, 2008;105:17504-9.*
Tranos et al. Clin Exp Ophthalmol 2006;34:226-32.*
Zhou et al. J Control Release 1998;55:281-95.*
Peyman et al. Ophthalmic Surg Lasers 1996:27:384-91.*
Charteris et al. Eye 2002;16: 369-374.*
Ito et al. Retina. 2005;25:1046-53.*
Immonen et al. Am J Ophthalmol 1996;122:870-4.*

(Continued)

Primary Examiner — Scott Long
(74) Attorney, Agent, or Firm — The Law Office of Patrick F. O'Reilly III, LLC

(57) ABSTRACT

A method to provide a therapeutic agent to an eye of a patient by implanting or inject a device that stably fits a particular location or position in the eye. The method thus provides agent inside the eye for a longer duration of agent release over a space-occupying area inside the eye.

14 Claims, 3 Drawing Sheets

(56) References Cited

OTHER PUBLICATIONS

Wikipedia: Inflammation 2018.*
Keskar et al. Tissue Engineering: Part A 2009;15:1695-1707.*
Pandey et al. J Cataract Refract Surg 2002;28:139-48.*
Nishi et al. J Cataract Refract Surg 1996;22:806-10.*
Youdim et al. Exp Neurobiol 2010;19:1-14.*
Zhou et al. Sci 2003;302:1215-7.*
Kudo et al. Ther Clin Risk Manag 2008;4:605-15.*
Ivayla Geneva (Int. J. Ophthalmol. "Photobiomodulation for the treatment of retinal diseases: a Review." 2016; 9(1): 145-152) (Year: 2016).*
Peyman, G., et al. Intravitreal injection of therapeutic agents, *Retina*. Jul.-Aug. 2009;29(7):875-912.
Peyman, G., et al. Intravitreal injection of liposome-encapsulated ganciclovir in a rabbit model. *Retina*. 1987;7(4)):227-9.
Khoobehi, B., et al. Clearance of sodium fluorescein incorporated into microspheres from the vitreous after intravitreal injection. *Ophthalmic Surg*. Mar. 1991;22(3):175-80.
Berger, et al. Intravitreal Sustained Release Corticosteroid-5-Fluoruracil Conjugate in the Treatment of Experimental Proliferative Vitreoretinopathy. *Investigative Ophthalmology & Visual Science*, Oct. 1996, vol. 37, No. 2, pp. 2318-2325.
Mello-Filho, P., et al. Helical intravitreal triamcinolone acetonide implant: a 6-month surgical feasibility study in rabbits. *Ophthalmic Surg Lasers Imaging*. Mar.-Apr. 2009;40(2):160-8.
Casey, D., et al. Analysis of responses to the Rho-kinase inhibitor Y-27632 in the pulmonary and systemic vascular bed of the rat. *Am J Physiol Heart Circ Physiol*. Jul. 2010;299(1):H184-92.
Ding, J., et al. Fasudil protects hippocampal neurons against hypoxia-reoxygenation injury by suppressing microglial inflammatory responses in mice. *J Neurochem*. Sep. 2010;114(6):1619-29.
Boé, D., et al. Acute and chronic alcohol exposure impair the phagocytosis of apoptotic cells and enhance the pulmonary inflammatory response. *Alcohol Clin Exp Res*. Oct. 2010;34(10):1723-32.
Yu, J., et al. Therapeutic potential of experimental autoimmune encephalomyelitis by Fasudil, a Rho kinase inhibitor. *J Neurosci Res*. Jun. 2010;88(8):1664-72.
Yin, H., et al. 2-methoxyestradiol inhibits atorvastatin-induced rounding of human vascular smooth muscle cells. *J Cell Physiol*. Mar. 2010;222(3):556-64.
Chiba, Y., et al. Synergistic effects of bone marrow stromal cells and a Rho-kinase (ROCK) inhibitor, Fasudil on axon regeneration in rat spinal cord injury. *Neuropathology*. Jun. 2010;30(3):241-50.
Zimering, M., et al. Autoantibodies in type 2 diabetes induce stress fiber formation and apoptosis in endothelial cells. *J. Clin Endocrin Metab*. Jun. 2009;94(6):2171-7.
Krawetz, R., et al. Human embryonic stem cells: caught between a ROCK inhibitor and a hard place. *Bioessays*. Mar. 2009;31(3):336-43.
Claassen, D., et al. ROCK inhibition enhances the recovery and growth of cryopreserved human embryonic stem cells and human induced pluripotent stem cells. *Mol Reprod Dev*. Aug. 2009;76(*):722-32.
Wataya, T., et al. Human pluripotent stem cell and neural differentiation. (Written in Japanese.) *Brain Nerve*. Oct. 2008; 60(10):1165-72.
Akhmetshina, A., et al. Rho-associated kinases are crucial for myofibroblast differentiation and production of extracellular matrix in scleroderma fibroblasts. American College of Rheumatology, vol. 58, No. 8, Aug. 2008, pp. 2553-2564.
Tanihara, H., et al. Intraocular pressure-lowering effects and safety of topical administration of a selective ROCK inhibitor, SNJ-1656, in healthy volunteers, Arch Ophthalmol, Mar. 2008; 126(3), pp. 309-315.
Kolavennu, V., et al. Targeting of RhoA/ROCK signaling ameliorates progression of diabetic nephropathy independent of glucose control. *Diabetes*. Mar. 2008;57(3):714-23.
Routhier, A., et al. Pharmacological inhibition of Rho-kinase signaling with Y-27632 blocks melanoma tumor growth. *Oncol Rep*. 23:861-867, 2010.
Thomas, S., et al. Src andCaveolin-1 reciprocally regulate metastasis via a common downstream signaling pathway in bladder cancer. *Cancer Res*. Dec. 10, 2010. [Epub. ahead of print.].
Liu, Y., et al. Serotonin induces Rho/ROCK-dependent activation of Smads 1/5/8 in pulmonary artery smooth muscle cells. *FASEB J*. Jul. 2009;23(7):2299-306.
Street, C., et al. Pharmacological inhibition of Rho-kinase (ROCK) signaling enhances cisplatin resistance in neuroblastoma cells. *Int J Oncol*. Nov. 2010;37(5):1297-305.
Yasuaki Hata, et al. Antiangiogenic Properties of Fasudil, a Potent Rho-kinase Indibitor, 52 Jpn. J Ophthalmol. (Feb. 16, 2008).
Yi Luo, et al. Cross-linked Hyaluronic Acid Hydrogel Films: New Biomaterials for Drug Delivery, 69 J Control. Rel. 169 (2000).

* cited by examiner

OPHTHALMIC DRUG DELIVERY METHOD

This application is a Continuation-in-Part of U.S. Ser. No. 13/457,568 filed Apr. 27, 2012; which is a Division of U.S. Ser. No. 12/985,758 filed Jan. 6, 2011; which is a Continuation-in-Part of U.S. Ser. No. 12/611,682 filed Nov. 3, 2009; which claims priority from U.S. Ser. No. 61/114,143 filed Nov. 13, 2008; each of which is expressly incorporated by reference herein in its entirety.

Figure 1:
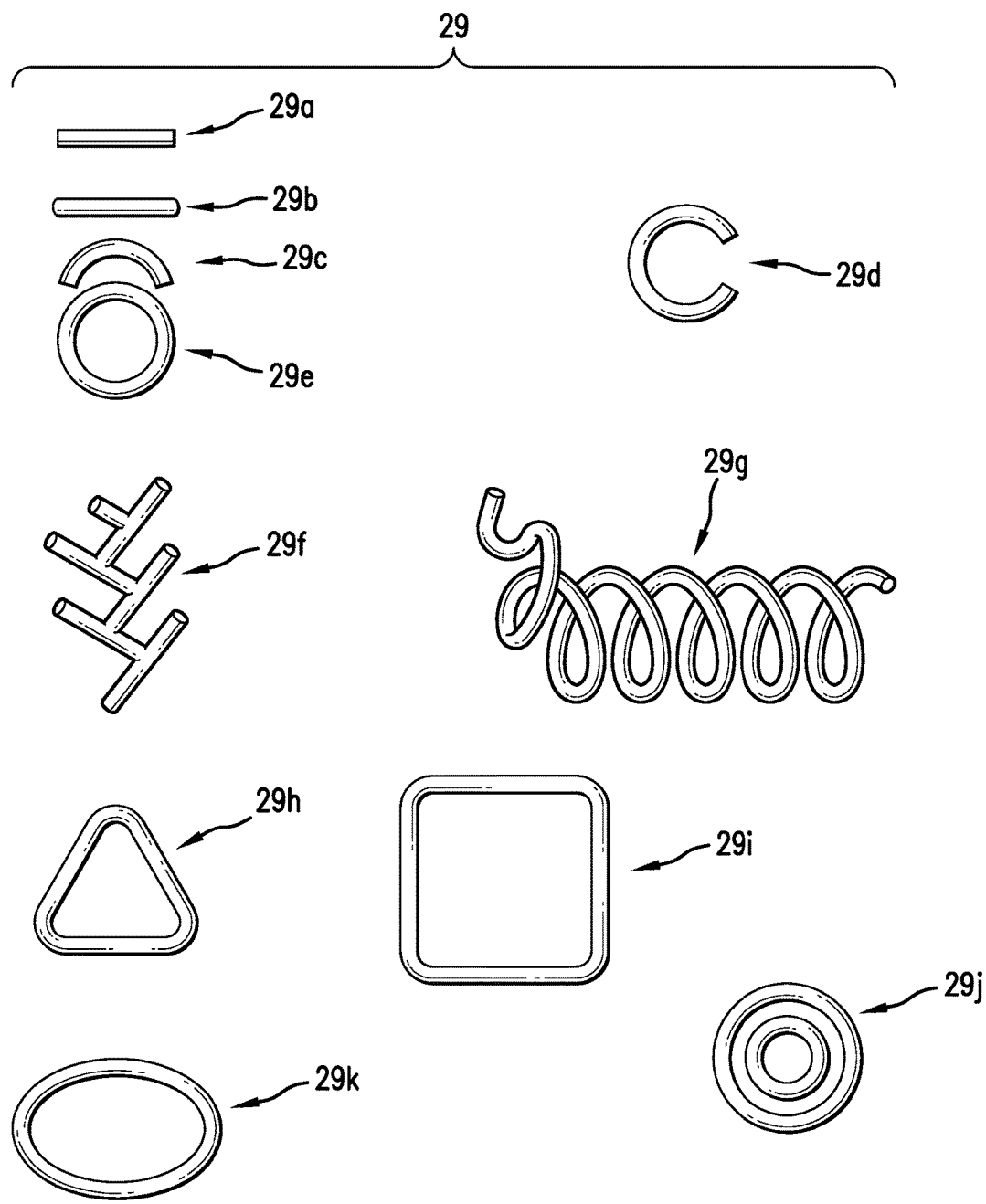
FIG. 1 shows embodiments of the device.
Figure 2A:
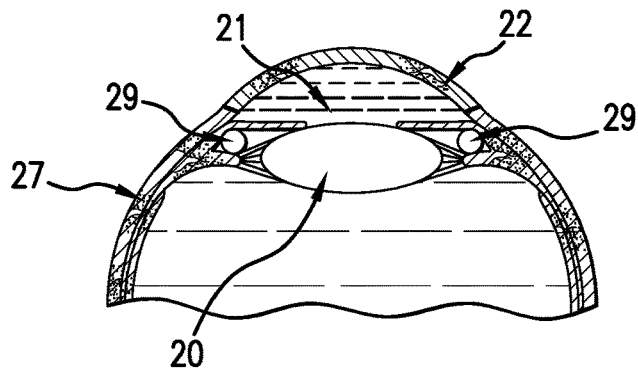
FIG. 2A shows a cross section of the lens capsule containing the pupil 21, cornea 22 and a device 29.
Figure 2B:
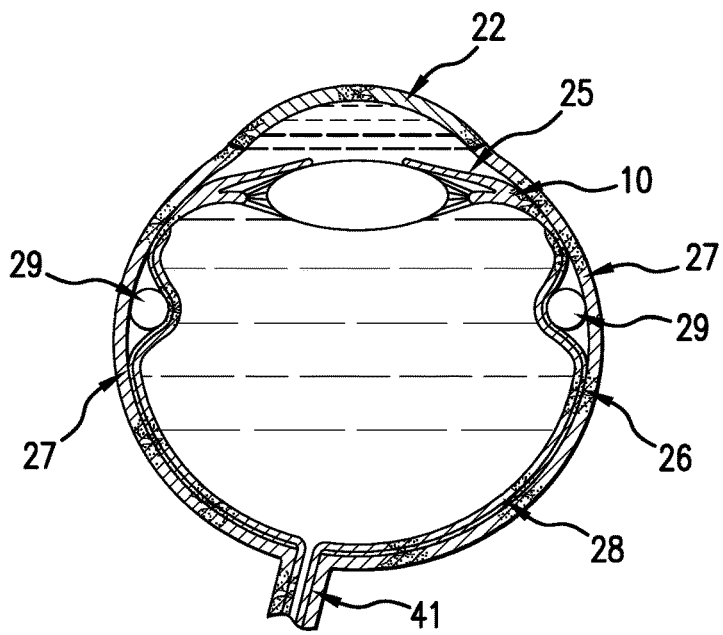
FIG. 2B shows a cross section of the eye depicting the supra choroidal space and the device 29 in relation to the cornea 22 and optic nerve 41.
Figure 2C:
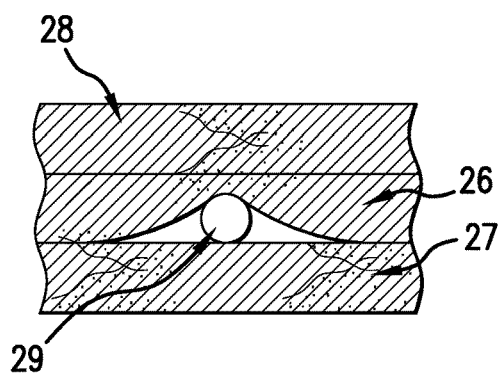
FIG. 2C shows a cross section of the eye wall.
Figure 2D:
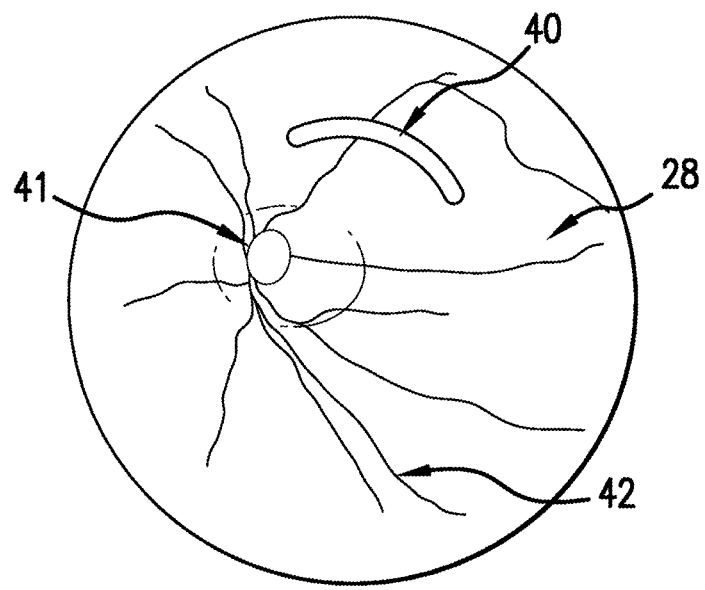
FIG. 2D shows a front view of the retina with optic nerve 41 and retinal vessels 42.
Figure 2E:
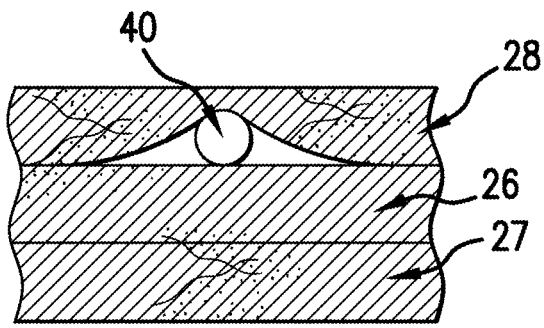
FIG. 2E shows the eye wall and subretinal implant 40.

Known methods of drug delivery to the eye have drawbacks, as the following illustrations demonstrate. Topical drug deliver must be repeated many times on a daily basis because of low or slow penetration. Compliance is also a problem. Subconjunctival drug delivery can be painful and has slow drug penetration. Intravitreal drug delivery has a short duration, typically of 2 to 30 days, so additional intervention and/or repeated injections are needed. The possibility of potential infections and retinal injury are also problems. Scleral implants and trans-scleral implants have not been attempted or tested. The implanted 29 devices usually are made of polymers; there is usually slow intraocular penetration when polymers are injected into the eye. The vitreous usually requires additional intervention with attendant potential complications, such as infection, retinal injury, etc.

Method of intraocular delivery of various therapeutic agents and methods are disclosed in Peyman et al., Retina, The Journal of Retinal and Vitreous Diseases 29 (2009) 875-912, which is expressly incorporated by reference in its entirety.

SUMMARY OF THE INVENTION

A method of treatment comprising providing a ROCK inhibitor to treat at least one of an ocular or neurodegenerative disorder using an implant device placed by implanting or an explant device placed by explanting in an eye of the patient in need of treatment, the device 15 mm to 60 mm in length; deformable; containing a ROCK inhibitor in at least one of a mucophilic preparation or nanoparticles or microparticles with a cell penetrating peptide; shaped to stably fit a suprachoroidal or subretinal position in the eye choroid, or on the lens zonules, or over the sclera under the conjunctiva; sized to occupy the choroidal space inside the eye, or the space on the lens zonules, or over the sclera, to provide a relatively longer duration of ROCK inhibitor release over a relatively larger space-occupying area inside the eye; and implanting or explanting the device in the eye. The nanoparticles may be coated with an antibody against a protein present in a neurodegenerative disease.

The device is placed suprachoroidially between the sclera and the choroid posteriorly with respect to the pars plana of the eye, subretinally following the curvature of the retina and subretinal space but not bulging the retina, in the vitreous cavity, in the intra-retina space, in the sub-retinal space, in the choroid, in the subconjunctival space anterior or posterior to insertion of eye muscles, implanted under the tenon capsule, implanted under the inferior conjunctiva, and/or in the inferior part of the limbus so the inferior part of the explant reaches the inferior cul de sac of the conjunctiva. The device releases the ROCK inhibitor, e.g., Fasudil, Ripasudil, RKI-1447, Y-27632, GSK429286A, Y-30141, etc. for 1 year-3 years at a rate of about 1 µg/day-5 µg/day. Agent release may range from 1 month up to 2 years at a rate of 1 µg/day-5 µg/day. The device containing a ROCK inhibitor may also contain an anti-vascular endothelial growth factor (VEGF), an anti-platelet derived growth factor (PDGF), an integrin inhibitor, a beta-blocker, an adrenergic agonist, a carbonic anhydrase inhibitor, a cholinergic agent, a prostaglandin analog, and/or a derivative of cannabinoid receptors.

The device may further contains stem cells, e.g., cultured stem cells, genetically modified stem cells, embryonic stem cells, mesenchymal stem cells, neuronal stem cells, pluripotent stem cells, glial stem cells, and/or stem cells having complement receptor 35. Cell penetrating peptides can extend the agent penetration to the posterior segment of the eye, anterior segment of the eye, or from the cornea to the retina. A mucophilic preparation can comprise chitosan, dendrimer, cell penetrating peptide (CPP), activated cell penetrating peptide, (ACPP), and/or hyaluronic acid. The implant or explant may be biodegradable or non-biodegradable.

Treatment may be for, e.g., age-related macular degeneration wet form, age-related macular degeneration dry form, diabetic retinopathy, retinitis pigmentosa, retinal artery occlusion, branch vein occlusion, central vein occlusion, macular edema, uveitis, and/or glaucoma. The patient may also be treated by ocular laser therapy. Treatment provides the patient with a non-toxic dose of a ROCK inhibitor by injecting into an eye of the patient at a site, e.g., through the pars plana, in the vitreous cavity, in an intra-retinal space, in a sub-retinal space, and/or in the choroid, or topically applying to the eye of the patient a formulation, e.g., nanoparticles, dendrimers, aptamers, and/or micelles. In one embodiment, the patient also receives laser therapy, where injection is either before or after laser application, and where the ROCK inhibitors are injected locally and/or applied topically to slow an inflammatory process while protecting non-laser treated areas of the retina. The ROCK inhibitor may be injected into the vitreous cavity at a concentration of 1 µg/ml to 1000 µg/ml in a slow release formulation, and may be in a formulation such as a solution, a polymer, an implant, microparticles or nanoparticles, and combinations thereof, further comprising poly(amidoamine) (PAMAM), poly(amidoamine-organosilicon) (PAMAMOS), poly(propyleneimine) (PPIO), poly(caprolactone), poly(lactic acid) (PLA), polylactic-co-glycolic acid (PLGA), tecto, multilingual, chiral, hybrid, amphiphilic, micellar, multiple antipen peptide, and Frechet-type dendrimers; functionalized microparticles or nanoparticles with an antibody and/or a ligand for a receptor or covalent coupling to one or more of cell penetrating peptides (CPP), arginine-CPP, cysteine-CPP, polyethylene glycol (PEG), biotin-streptavadin, and/or acetyl cysteine. In one embodiment, the ROCK inhibitor is in nanoparticles sized to pass through the intercellular space of the retina and accumulate under the retina, therefore being effective both for retinal and choroidal disease processes affecting each of the retina and choroid.

Stem cells may be injected to replace the loss of endothelial cells and normalize the function of the perifoveal capillaries in patients with diabetic macular edema associated with vascular leakage, demonstrable deep retinal vascular deformation or loss, age related macular degeneration, glaucoma, and retinal ischemia either centrally or peripherally. Stem cells may be administered at a concentration of about 5-100,000 stem cells having complement receptor 35 (CD 35) in combination with ROCK inhibitors. The method results in one injection per month reduced to one injection per at least six months.

One embodiment is a method of treating glaucoma, e.g., open angle glaucoma, low tension glaucoma, and/or an optic nerve disorder, by providing an anti-glaucoma agent using a device implantable in an eye of the patient in need of treatment, the device 5 mm to 60 mm in length; deformable; containing an anti-glaucoma agent in at least one of a mucophilic preparation or nanoparticles or microparticles with a cell penetrating peptide, optionally in a formulation selected from the group consisting of a solution, a polymer, an implant, microparticles or nanoparticles, and combinations thereof, further comprising poly(amidoamine) (PAMAM), poly(amidoamine-organosilicon) (PAMAMOS), poly(propyleneimine) (PPIO), poly(caprolactone), poly(lactic acid) (PLA), polylactic-co-glycolic acid (PLGA), tecto, multilingual, chiral, hybrid, amphiphilic, micellar, multiple antipen peptide, and Frechet-type dendrimers; functionalized microparticles or nanoparticles with an antibody and/or a ligand for a receptor or covalent coupling to one or more of cell penetrating peptides (CPP), arginine-CPP, cysteine-CPP, polyethylene glycol (PEG), biotin-streptavadin, and/or acetyl cysteine; shaped to stably fit in the subconjunctival space anterior or posterior to the insertion of the eye muscles as a string to release the agent through the sclera to provide a relatively longer duration of anti-glaucoma agent release over a relatively larger space-occupying area inside the eye; and implanting the device in the eye. The mucophilic preparation can include microparticles, nanoparticles, chitosan, and/or hyaluronic acid. The cell penetrating peptide extends the agent penetration to the posterior segment of the eye. A curved spatula may be inserted through a surgically created incision in the conjunctiva. The spatula is advanced 180 degrees around the sclera from the superior or inferior side, the retrieved though the same conjunctival incision in the lower side. The device is placed in the space created by the curved spatula, providing extended drug delivery. Implanting may be under the tenon capsule, inside the choroid, or inside the eye. The device releases the anti-glaucoma agent for 1 year-3 years at a rate of about 1 µg/day-5 µg/day, and may further contain stem cells. The anti-glaucoma agent may be a ROCK inhibitor, a beta-blocker, an adrenergic agonist, a carbonic anhydrase inhibitor, a cholinergic agent, a prostaglandin analog, a derivative of a cannabinoid receptor, and combinations thereof. The implant may be biodegradable or non-biodegradable, and may release the agent at a constant rate of 10 µg/day-50 µg/day to provide the agent to the patient for at least six months. An implant containing an agent not tolerated by the patient may be removed and replaced with an implant containing a different agent. The implant may treat glaucoma's neurodegenerative effects on survival of the retinal ganglion cells (RGC) and their nerve fiber layer (NFL) if intraocular pressure is not adequately controlled.

One embodiment is a method of treatment by providing stem cells to treat an ocular or neurodegenerative disorder using an implant device placed by implanting or an explant device placed by explanting in an eye of the patient in need of treatment, the device 5 mm to 60 mm in length; deformable; containing stem cells in at least one of a mucophilic preparation or nanoparticles or microparticles with a cell penetrating peptide; shaped to stably fit a suprachoroidal or subretinal position in the eye choroid, or on the lens zonules, or over the sclera under the conjunctiva; sized to occupy the choroidal space inside the eye, or the space on the lens zonules, or over the sclera, to provide a relatively longer duration of stem cell release over a relatively larger space-occupying area inside the eye; and implanting or explanting the device in the eye. The stem cells may be cultured stem cells, genetically modified stem cells, embryonic stem cells, mesenchymal stem cells, neuronal stem cells, pluripotent stem cells, glial stem cells, stem cells having complement receptor 35, and combinations thereof.

The disclosed system and method uses the capsular bag, obtained during or after cataract extraction, as a polymeric slow release drug delivery system and method. It is used for drug delivery and for simultaneous support for the lens capsule.

The inventive system is used during or after intra-ocular surgery for cataract extraction in the same session. After an opening in the anterior chamber is made, a circular area of the anterior capsule is removed to extract the lens cortex and nucleus.

In one embodiment, the system and method is used post-surgically to prevent or to treat inflammation. After surgery, most if not all eyes have some inflammation for which treatment is administered. For example, all patients who have diabetic retinopathy have post-surgical ocular inflammation. All patients who have a previous history of uveitis have more excessive inflammation.

In one embodiment, the device 29 is a capsular ring of any size configured in a shape for implanting outside the crystalline lens 15. Thus, the device is not dependent on removal of the crystalline lens 15. In this embodiment, the device 29 is intraocular but is extralens, it is external to the lens. It is supported in the eye by the lens zonules or ciliary body 10.

In one embodiment, the device 29 is a capsular ring of any size configured in a shape for implanting over the lens capsule having an intraocular lens 20. In this embodiment, where the eye contains an intraocular lens 20, the device is configured for implanting between the iris 25 and the outer part of the lens capsule.

It is important that the device 29 shape fits its position, that is, its location, inside the eye. The length of the device fits a large space inside the eye, and provides a longer duration of agent release over a wider area inside the eye than known devices.

In one embodiment, the device 29 is configured for implanting anterior to the lens 15. In this embodiment, the device is configured either C-shaped 29d or ring shaped 29e to lay on the zonules or the anterior lens capsule or the intraocular lens (IOL) 20. Any other device shape would not be stable in this position, that is, this location.

In one embodiment, the device 29 is configured for implanting in the choroid 26. In this embodiment, the device is configured either as a rod 29a or as a snake-shaped semicircle 29c. In these configurations, the device follows the inside curvature of the sclera 27 and can readily snake inside the suprachoroidal space. Any other device shape would be difficult to configure in the suprachoroidal space, and could penetrate the choroid 26 and the retina 28 resulting in serious complications. Any other device shape may not sufficiently large to cover a relatively large area.

In one embodiment, the device 29 is configured for implanting under the retina 28, that is, for subretinal implantation. In this embodiment, the device is configured either as a rod 29a or as a semicircle 29c, following the curvature of the retina and the subretinal space. Although a circular device may be implanted under the retina 29, implanting would be difficult. A circular device would not follow the retinal curvature and would bulge the retina.

In all embodiments the device is biodegradable, also termed bioabsorbable; no foreign body remains in the eye after the device is absorbed.

FIG. 1 shows various embodiments of the device 29. The device is rod shaped 29a, 29b and may be straight, curved 29c, C-shaped 29d, closed loop 29e, Its length ranges from 1 mm to 60 mm inclusive. In one embodiment, its length ranges from 15 mm to 600 mm inclusive. Its diameter ranges from 30 micrometers to 3 millimeters inclusive and is round, flat, bead-shaped, etc. The device is made of biodegradable polymers that contain and release agent contained within the device and/or within the polymers. In one embodiment the device is solid. In one embodiment the device is not-solid. In either embodiment, the device may be sized to be between 8 mm diameter and 18 mm diameter, inclusive.

The device 29 is shaped as a rod 29a, tube 29b, open loop 29c, 29d or closed loop 29e. In embodiments where the device is a rod 29a, the device can be a solid rod or a hollow tube with closed ends. The device is folded for easy implanting through an incision that is as small as 1 mm. The nanlded over the lens capsule in the posterior chamber. For implanting, a viscoelastic substance is also implanted for lubrication and ease of implantation, as known to one skilled in the art. Once the device is it in place, the device is unfolded.

For a suprachoroidal implantation application, the device 29 is shaped as a rod 29a, tube 29b or open loop 29c, 29d. It is not shaped as a closed loop. The device is implanted under the sclera 27 over the ciliary body 10 or the choroid 26 of the eye through a small incision, preferably in the sclera 27 at the plars plana area 1 mm to 4 mm behind the limbus of the cornea/sclera junction, or anywhere else in the sclera 27. The incision reaches the ciliary body 10/choroid 26. The space between the ciliary body 10/choroid 26 and the sclera 27 is called suprachoroidal space. The device which has a semicircular 29c, 29d or straight rod 29a configuration is threaded in the suprachoroidal space in any desired direction toward any meridian. The resilient structure of the device assists in moving it in this space to the desired length. Because of its round tip, it cannot penetrate the choroidal vessels but follows the suprachoroidal space when pushed against the resilient sclera. Its location can also be verified by indirect ophthalmoscopy. After the implantation, the scleral incision is closed with a suture.

For a subretinal implantation application, the device 29 is shaped as a rod 29a, tube 29b, or semicircle 29c. The device is implanted through a pars plana vitrectomy through the sclera 27. A subretinal bleb is created using a balanced saline solution at the desired retinal location, e.g., in the superior retina. Using forceps, the device 29 is inserted gently into the subretinal space where it remains until it is adsorbed. It is known that material injected under the retina 28, with time, diffuses from that location into the subretinal space under the macula and exerts a therapeutic effect.

Implantation methods are known to one skilled in the art. Implantation may use forceps. Implantation may use an injector.

In one embodiment, the device 29 contains agents that are neuronal cell protective and/or neuronal cell proliferative. The agents can be on the device, in the device, both on and in the device, and/or administered with the device by, e.g., simultaneous or substantially simultaneous injection upon implantation. Such devices are used for implanting in patients with glaucoma, neurodegenerative diseases including dry or wet forms of age related macular degeneration (ARMD), retinitis pigmentosa where the retinal cells and retinal pigment epithelial cells die by aging and genetic/inflammatory predisposition, and diabetic retinopathy.

One non-limiting example of such an agent is rho kinase (ROCK). ROCK plays an important role in cell proliferation, cell differentiation and cell survival/death. Blockade of ROCK promotes axonal regeneration and neuron survival in vivo and in vitro, thereby exhibiting potential clinical applications in spinal cord damage and stroke. ROCK inhibitors attenuated increases in pulmonary arterial pressures in response to intravenous injections of serotonin, angiotensin II, and Bay K 8644. Y-27632, sodium nitrite, and BAY 41-8543, a guanylate cyclase stimulator, decreased pulmonary and systemic arterial pressures and vascular resistances in monocrotaline-treated rats.

Its use to prevent and/or treat in degenerative retinal diseases such as ARMD, retinitis pigmentosa, and glaucoma has not been reported and thus is new. ARMD can have an inflammatory component, contributing to cell death and apoptosis. Oxidative and ischemic injury in ARMD and diabetic retinopathy also contributes to ROCK activation. Because ROCK plays an important role in these processes, inhibiting ROCK can prevent neuronal cell death.

In one embodiment, ROCK inhibitors are injected directly into the eye, e.g., in the vitreous cavity, under the retina 28, under the choroid 26, etc. Methods and formulations are disclosed in the following references, each of which is expressly incorporated by reference in its entirety: Peyman et al. Retina 7 (1987) 227; Khoobehi et al., Ophthalmic Surg. 22 (1991) 175; Berger et al., Investigative Ophthalmology & Visual Science, 37 (1996) 2318; Berger et al., Investigative Ophthalmology & Visual Science, 35 (1994) 1923. In one embodiment, ROCK inhibitors are injected in a polymeric formulation to provide a slow release system. In this embodiment, the polymeric material is made from any biodegradable polymer as known to one skilled in the art. Examples of suitable materials include, but are not limited to, polymers and/or co-polymers (poly)lactic acid (PLA), (poly)glycolic acid (PGA), lactic acid, (poly)caprolactone, collagen, etc. These can be injected or implanted in a shape and location as described above. In one embodiment, ROCK inhibitors are administered in a slow release system.

In one embodiment, ROCK inhibitors are administered with one or more other agents that inhibit inflammatory processes, inhibit angiogenesis, and/or inhibit fibrosis. Such agents include, but are not limited to, vascular endothelial growth factor (VEGF) inhibitors, platelet-derived growth factor (PDGF) inhibitors, and integrin inhibitors. In one embodiment, ROCK inhibitors are administered in a non-slow release form, and VEGF, PDGF, and/or integrin inhibitors are administered in a slow release form. In one embodiment ROCK inhibitors are administered in a slow release form, and VEGF, PDGF, and/or integrin inhibitors are administered in a non-slow release form. In one embodiment, ROCK inhibitors and VEGF, PDGF, and/or integrin inhibitors are administered in a dual, triple, or quadruple slow release form.

Examples of ROCK inhibitors include, but are not limited to, the following agents: fasudil hydrochloride (inhibitor of cyclic nucleotide dependent- and rho kinases); GSK 429286 (a selective ROCK inhibitors); H 1152 dihydrochloride (a selective ROCK inhibitor); glycyl-H 1152 dihydrochloride (a more selective analog of H 1152 dihydrochloride); HA 1100 hydrochloride (a cell-permeable, selective ROCK inhibitor); SR 3677 hydrochloride (a potent, selective ROCK inhibitor); Y 39983 dihydrochloride (a selective ROCK inhibitor); and Y 27632 dihydrochloride a selective p160 ROCK inhibitor). VEGF inhibitors include, but are not limited to, Avastin, Lucentes, etc. PDGF inhibitors include, but are not limited to, Sunitinib. Integrin inhibitors are known to one skilled in the art.

The concentration of ROCK inhibitor is administered so that its concentration upon release ranges from less than 1 micromol to 1 millimole. In one embodiment, the concentration of agent is administered so that its concentration upon release ranges from 1 micromole/day to 100 micromol day. Such concentrations are effective and are non-toxic.

Inhibitors of the enzyme rho kinase (ROCK), i.e., ROCK inhibitors, are used for therapy in three ocular disease processes: age related macular degeneration (ARMD), both wet and dry forms, diabetic macular edema (DME), and glaucoma. The inventive method uses ROCK inhibitors to treat these ocular diseases, as well as neurodegenerative diseases, e.g., Alzheimer's disease and traumatic brain injuries. In the inventive method, ROCK inhibitors may be used alone or, in another embodiment, may be used in combination with stem cell delivery.

ARMD is one of the leading cause of blindness among individuals beyond the age of 55 years, affecting over 1.8 million people. The dry form of ARMD manifests as gradual loss of central vision, associated by formation of drusen under the retinal pigment epithelium (RPE) which leads to degeneration of RPE, photoreceptors, and the choriocapillaries. Unfortunately, until now, there is no effective treatment for this process. It is considered that genetic predisposition and some environmental factors influence its progression. The wet form of ARMD affects about 200,000 patients in the United States. It is associated with sudden loss of central vision caused by accumulation of drusen followed by abnormal proliferation of vessels in the choroid, i.e., neovascularization, that penetrate Bruch's membrane under the RPE and enter the sub-retinal space, cause leakage of fluid from these vessels and bleeding. Subsequently, scar tissue replaces normal retinal structures in the macula.

The current treatment strategy for both wet and dry forms of ARMD is to administer inhibitors of vascular endothelial growth factor (VEGF). VEGF inhibitors inhibit the abnormal ischemic tissue in the retina and choroid; this, in turn, inhibits growth of the neovascular tissue. Unfortunately, patients receiving VEGF inhibitors must be treated invasively, and on a monthly basis, by intravitreal injections of various anti-VEGF agents. Even with treatment, in many cases of wet or dry forms of ARMD, the lost tissues are not regenerated and vision cannot be improved beyond a certain level.

Numerous inflammatory processes activate Rho/ROCK signaling and nitric oxide synthase. Increased RHO/ROCK activity enhances vascular inflammatory diseases such as atherosclerosis, vascular lesions, vascular permeability, and cell proliferation and occlusion, along with activation of platelet growth factors (PDGF) and inhibition of proteolysis.

Rho kinase (ROCK) is an enzyme that acts on the cytoskeleton and thus regulates cellular shape, gene expression, proliferation, motility, tight junction integrity, depolymerization of actin filaments, protein oligomerization, cellular contractibility, vascular tone, inflammation, and oxidative stress increasing the amount of collagen. Inhibitors of rho kinase, also termed rho-associated protein kinase inhibitor, ROCK inhibitor) are downstream targets of ROCK. Examples of ROCK inhibitors include Fasudil, Ripasudil, RKI-1447, Y-27632, GSK429286A, and Y-30141, etc.

ROCK inhibitors are downstream targets of ROCK that play important roles in atherosclerosis and hypertension. ROCK signaling is involved in many vascular and neurodegenerative diseases, such as Parkinson's disease, Alzheimer's disease, diabetes, heart disease, uveitis, and cancer, by blocking cell migration and spreading. ROCK inhibitors act as an angiostatic agent, and can be administered alone, or can be administered and work synergistically with anti-VEGF agents such as Bevacizumab, Ranibizumab, Aflibercept, Avastin, and anti-platelet derived growth factor (PDGF) agents.

In one embodiment, a non-toxic dose of a ROCK inhibitor, such as Fasudil etc., is administered directly into the eye with a small gauge needle through the pars plana located about 3 mm behind the cornea. In one embodiment, a non-toxic dose of a ROCK inhibitor, such as Fasudil etc., is injected in the vitreous cavity by injection through the pars plana. In one embodiment, the dose for intravitreal injection in a physiological solution can be at concentration of 1 µg/ml to 1000 µg/ml or more.

In one embodiment a ROCK inhibitor, such as Fasudi etc., is administered in solution. In one embodiment a ROCK inhibitor, such as Fasudil etc., is administered as previously described as a slow release polymer, e.g., polycaprolactone, PLA/PGLGA, as an implant, e.g., porous silicone, that is implanted either in the suprachoroidal space or implanted over the lens zonules, and/or as microparticles or nanoparticles in the vitreous cavity. In an embodiment using an implant, the implant may be non-biodegradable, and in use may be removed after medication is depleted. In an embodiment using nanoparticles, the nanoparticles advantageously may pass through the intercellular space of the retina and accumulate under the retina, therefore being effective both for retinal and choroidal disease processes such as wet ARMD and inflammatory diseases affecting both structures.

In one embodiment the nanoparticles include dendrimers, aptamers, and/or micelles administered in solution on the cornea, and/or injected into the conjunctiva or subconjuctiva, injected intravitreally, etc. Such nanoparticles are known in the art, as only one non-limiting example, dendrimers include poly(amidoamine) (PAMAM), poly(amido-amine-organosilicon) (PAMAMOS), poly(propyleneimine) (PPIO), tecto, multilingual, chiral, hybrid, amphiphilic, micellar, multiple antipen peptide, and Frechet-type dendrimers. The nanoparticle can be functionalized to render or enhance its biocompatibility, and can be further treated or delivered to enhance cell penetration. An antibody and/or a ligand for a receptor may be employed to enhance biocompatibility, association with, or covalent coupling to one or more of cell penetrating peptides (CPP), arginine-CPP, cysteine-CPP, polyethylene glycol (PEG), biotin-streptavadin, and/or acetyl cysteine. The nanoparticle size varies from 1 micron to 990 microns depending on its use and application in different part of the eye and elsewhere.

It will be appreciated that the method may be used in conjunction with administration of other agents, e.g., anti-VEGF agents, steroids, non-steroidal antiinflammatory drugs, etc., and may be used to treat patients with ARMD as either a single therapy or in conjunction with laser application. The inventive method may also be used to treat other ocular pathologies such as but not limited to retinal artery occlusion, branch vein occlusion, central vein occlusion, diabetic retinopathy, etc.

In one embodiment ROCK inhibitors are used in a slow release delivery polymer, such as PLGA, PLA, (poly)caprolactone, etc. conjugated with chitosan combined with a slow release polymer. In one embodiment, the polymer may be coated on a microparticle or nanoparticle. In one embodiment, the dose as a slow release medication due to the polymer coating can be 1 µg/day to 10 µg/day or more. In one embodiment, PLGA, PLA, dendrimer, etc. coated nanoparticles may contain antibodies against the amyloid or Tau plaques found in Alzheimer's disease, for targeted therapy. In one embodiment, the ROCK inhibitor in a physiological solution formulated with a microsphere or nanoparticle carrier is administered under the subconjunctival space for extended delivery. In one embodiment, the ROCK inhibitor is injected in a slow release form as previously described, or is injected in the choroid and/or subconjuctivally in solution. In one embodiment, the ROCK inhibitor is provided in a slow release (poly)caprolactone implant. In one embodiment, the ROCK inhibitor is administered in a physiological solution, or a microsphere, or a nanoparticle carrier under the subconjunctival space to provide sustained delivery over a period of time.

In one embodiment administration as nanoparticles such as dendrimers with cell penetrating agents as A solution on the conjunctiva or subconjunctiva enhances penetration of the ROCK inhibitor to the posterior segment, such as the choroid and retina.

As therapy for early ARMD, ROCK inhibitors may be injected intravitreally, supra-choroidally, or subretinally as needed, either alone, with nanoparticles, and/or with polymers for extended delivery in the vitreous cavity to reach the RPE through the intercellular spaces of the retina. ROCK inhibitors may also be administered topically for ARMD in general, either alone or in a mucophilic preparation such as chitosan and/or CCP and ACCP agents to provide an extended effect.

In one embodiment, the ROCK inhibitor is administered in conjunction with other agents, including but not limited to dexamethasone, anti-VEGF agents, and/or anti-PDGF agent, noting that ROCK inhibitors such as Fasudil also have an anti-PDGF effect that would ameliorate the subsequent tissue fibrosis seen when anti-VGEF agents are used alone.

In one embodiment, ROCK inhibitors alone or in combination with anti-VEGF or anti-PDGF agents can reestablish the retinal and choroidal microvasculature in diseases, eliminate drusen in ARMD and eliminate amyloid deposits within drusen.

In one embodiment the therapeutic approach involves the use of ROCK inhibitors with or without simultaneous stem cell therapy. Stem cells may be embryonic stem cells, mesenchymal stem cells, or neuronal stem cells. The stem cells are grown in vitro with or without modification of their genetic components using CRISPR-cas, which may edit the stem cells in the form of gene knock-out and/or gene alteration using Non-Homologous End Joining (NHEJ) or Homology Directed Repair (HDR), where the CRISPR-cas is directed to the genetic site of interest by a guide RNA and a cas protein cleaves the target DNA. The stem cells and ROCK inhibitors may be administered together in an implant, e.g., a tube-shaped implant, as previously described or injected in the vitreous cavity, intraretinally, or subretinally. The stem cells and ROCK inhibitors may be administered intravenously or by injection into the cerebrospinal fluid. The stem cells and ROCK inhibitors may be administered as solution intranasally as a drop or spray to reach the olfactory nerve in Alzheimer disease or in traumatic brain injuries. In one embodiment, ROCK inhibitors are incorporated into polymeric slow release nanoparticles such as dendrimer PLA, PGL, dendrimers etc., and administered along with stem cells, as previously described.

The release form of the active, i.e., microspheres, nanoparticles, implant, etc. in any of several embodiments of each (e.g., with polymers, coatings, etc.) can be located in various regions or parts of the eye to slowly release the medication to the desired area of the retina. Such a sustained slow release delivery can have a controllable duration depending upon the specific type of formulation. Such a duration may range from a few months to a few years, e.g., 3 months to 3 years, or even longer. As only one, non-limiting example, a ROCK inhibitor such as Fasudil is released from an implant at a rate of 1 µg/day-5 µg/day or more, for a period of 1 year-2 years.

In one embodiment, a patient has dry ARMD with drusen with a probable sub-clinical inflammatory process. In this embodiment, administration of any of the previously described embodiments of ROCK (e.g., in a polymeric form, as nanoparticles, as microparticles, with or without stem cells, etc.), prevents progression or slows nerve degeneration. In one embodiment, the inventive method may be applied to patients suffering from the occult form of wet ARMD associated with minimal vascular leakage, and may provide advantages such as prevent or delay onset.

It is known that an overt inflammatory process is destructive to the bodily tissues and organs. However, and contrary to this knowledge, controlled induced inflammation by laser spot application using low to moderate energy at selective areas of the retina, both eliminated part of the ischemic retinal area and also stabilized the retina against further inflammatory ischemic processes.

In one embodiment, a localized sub-clinical inflammation in the retina and/or retinal pigment epithelium (RPE) is created using low power laser spots below a threshold of producing a visible retinal burn. For example, one can apply the standard ophthalmic units used in laser coagulation at low power femtosecond or longer duration of pulses at a frequency up to 1 Hz of any visible or invisible wavelength of 400-1300 nm, with a spot size of about 20 µm to 1 mm under observation of the retina. This sub-clinical, or very low grade, inflammation induces release factors that attract various cells to remove the tissue debris and to induce repair. These localized release factors can also be used to attract endogenous and administered thousands of stem cells, e.g., pluripotent stem cells, glial and neuronal stem cells, and ROCK inhibitors would then be introduced into the vitreous cavity, intra-retinal space, or sub-retinal space to replace the loss of RPE cells. In one embodiment, embryonic stem cells and/or genetically modified stem cells, glial and neuronal stem cells, are added to achieve this result. In one embodiment where the patient has ARMD with drusen, in selective area of the macula the laser is applied with 10 µm-100 µm spot size near the drusen without producing a visible burn in the RPE. The lesions may be further rendered visible by fluorescence angiography, OCT angiography, etc.

In one embodiment following laser application, both stem cells and ROCK inhibitors in a solution or as particles, e.g., microspheres, nanoparticles, etc. are injected and/or implanted. If injected, the components may be injected in any of several ocular sites, e.g., in the vitreous, intra-retinal space, sub-retinal space, in the choroid using polymers, etc. If implanted, the components are implanted in the vitreous, intra-retina space, sub-retinal space, in the choroid, etc. Implants may release the component for 1 year-3 years at a rate of about 1 µg/day-5 µg/day.

In one embodiment, either before or after laser application, ROCK inhibitors are either injected locally in different part of the retina and choroid or in the vitreous cavity to slow the inflammatory process, while protecting the rest of the retina without having the side effects of drugs such as steroids, NSAIDs, etc.

Macular edema is frequently seen with patients having Type II diabetes as a complication of diabetic vascular disease. Macular edema can also result after acute or chronic untreated ocular inflammation, as a response to a systemic immune disease, or in uveitis, infection, after a contusion or penetrating injury of the eye, and after ocular surgery. Diabetic macular edema (DME) is defined by swelling of the central retina fovea in diabetic patients. It occurs with 10-50% of diabetic patients diagnosed with diabetes for 3-5 years, i.e., older diabetic patients. DME is associated with loss of endothelial cells, where vascular occlusion causes slow leakage in the retina or sub-retinal space and loss of nerve fibers, resulting in reduced vision. Its hallmark is leakage from the perifoveal capillaries, elevating the fovea to about at least 1.5 mm (one optic disk diameter), contributing to a significant visual loss in this patient population. Symptoms are produced by elevation of the central fovea to about 500 micron as diagnosed by optical coherence tomography (OCT). Diagnosis is by retinal examination, OCT, fluorescein angiography, or optical coherence angiography (OCA). Visual acuity may not be reduced in very early stages of the disease, it later is the major complaint in diabetic patients suffering from this complication of diabetes.

Therapy for DME is directed toward reducing the vascular permeability and vascular abnormalities seen in the macular area. Interestingly, loss of the retinal capillaries in the retinal periphery may also cause or enhance the edema and the symptom of DME in the central retina. Past clinical studies have demonstrated that limited application of laser coagulation in the macular area can reduce the macular edema and improve the function in about 50% of the patients. This treatment in general has been useful, but cannot be repeated because it damages the retina and RPE, forming scar tissues that affect central vision. Loss of pericytes, contractile cells that wrap around the endothelial cells of capillaries, is another important factor in leakage of the perifoval capillaries. Anti-VEGF medications have been administered by intravitreal injection, reducing the amount of VEGF produced from the ischemic retina and significantly reducing macular edema. Undesirably such medications must be injected in the eye almost every month to keep edema in check. Such monthly injections into the eye are very uncomfortable for patients and have potential complications such as infections, etc. It is also a serious financial burden to patients; these medications are expensive, costing more than $2,000 per injection and even the copayments often pose a financial burden. Steroids are useful and work synergistically with anti-VEGF medications, but intravitreal administration of steroids cause two major complications: one is cataract formation in about 90% of the patients, and the other is glaucoma formation in more than 50% of the patients; both complications require surgical intervention for treatment.

The inventive method ameliorates these problems. Moreover, it may be repeated if needed, e.g., if signs of DME returns. ROCK inhibitors such as Fasudil, etc., can be injected intravitreally or in the choroid in an early stage of the disease process to stabilize the vascular condition of the perifoveal capillaries. In one embodiment, the ROCK inhibitors are administered alone or in a nanoparticle formulation with slow release agents such as (poly)caprolactone, PLA, PGLA, dendrimers, etc. coated with cell penetrating peptides (CPP or achievable CPP, ACPP) for enhanced cell penetration. This solution can also be applied superficially on the eye, cornea, conjunctiva, or can be injected. This embodiment significantly reduces the number of injections, e.g., a required one injection per month may be reduced to one injection per six months, or even longer than six months. In one embodiment, the rate of the release of ROCK inhibitor can lasting for 6 weeks-8 weeks when administered at a concentration of 10 µg/0.1 ml-200 µg/0.1 ml of physiological solution. In one embodiment, ROCK inhibitors are administered intravitreally in a volume of 0.05 ml with anti-VEGF; the concentration of ROCK inhibitors ranges from 10 µg-40 µg, and the concentration of anti-VEGF agents ranges from 500 µg-1 mg. This embodiment not only enhance the effects of the anti-VEGF agents, but also eliminates the need for a monthly injection, prolongs the therapeutic effect of each of the ROCK inhibitors and anti-VEGF agents, and not increase intraocular pressure.

In one embodiment, intravitreal administration is either preceded by or subsequent to laser therapy to increase the potential of both treatments in stabilizing the retinal vascular disease and having a more lasting therapeutic effect on vascular leakage.

In one embodiment, a slow release formulation of ROCK inhibitors is administered with stem cells or genetically modified endothelial cells, etc. at a concentration of about 50-100,000 stem cells having complement receptor 35 (CD 35) to replace the loss of endothelial cells etc. and normalize the function of the perifoveal capillaries. This embodiment may also be effectively applied to patients with DME associated with vascular leakage, demonstrable deep retinal vascular deformation or loss, and retinal ischemia either centrally or peripherally, with release of cytokines that induce VEGF production and vascular leakage.

In one embodiment, a ROCK inhibitor is administered in DME as a topical medication. The ROCK inhibitor may be administered alone, or may be administered in a mucophilic preparation such as chitosan or hyaluronic acid or dendrimer nanoparticles to provide a long lasting effect. In one embodiment, a ROCK inhibitor is administered in diabetic macular edema as a topical medication. The ROCK inhibitor may be administered alone, or may be administered in a mucophilic preparation such as chitosan or hyaluronic acid to provide a long lasting effect, or may be administered as nanoparticles such as dendrimers along with cell penetrating peptides (CPP or ACPP) to reach the posterior segment of the eye.

Glaucoma is a disease that affects the eye and is considered as one of the major causes of blindness. There are many forms of glaucoma, having different pathogenesis. Among these are open angle glaucoma (OAG), where the anterior chamber located between the cornea and the iris is open, closed angle glaucoma where the anterior chamber angle is closed, and secondary glaucoma caused by different etiologies but often an inflammatory process proceeds its occurrence. Glaucoma can be congenital or acquired, with a genetic predisposition in some patients.

Regardless of its pathogenesis, the hallmark of glaucoma is an increased intraocular pressure (IOP) except for low tension glaucoma where the IOP appears to be normal but the patient has other symptoms of glaucoma. A characteristic finding in glaucoma is cupping of the optic nerve head and loss of the retinal nerve fiber layer and ganglion cells. These lead, or may be considered a consequence of, a degenerative process potentially affecting retinal ganglion cells, an imbalance of the IOP, and intracranial pressure leading to gradual loss of visual field that can be constricted or completely lost with time. There are many treatment modalities in managing the disease processes. Since the IOP is, in most cases, elevated beyond a normal level of 10-20 mmHg, routine IOP monitoring, including potentially a 24 hour or more measurement of these values (during the day and night) is required to determine any pressure variations, particularly during sleep where the IOP generally is raised. This can compromise the retinal nerves and retinal circulation, even if the pressure is within a normal range of 10-20 mm Hg, such as in in patients with low tension glaucoma.

Glaucoma treatment is mostly medical, i.e., applying anti-glaucoma medication(s) as eye drops to reduce the intraocular pressure. Medications that decrease the amount of fluid to be produced in the eye are so-called beta-blockers such as Betagan or Timoptic, adrenergic agonists such as Alphagan, carbonic anhydrase inhibitors such as Azopt, Diamox, and Trusopt. There are also medications that increase fluid drainage from the eye including cholinergic medications such as pilocarpine and phospholine, and prostaglandin analogs such as Lumigan and Xalatan. Such medications are applied using eye drops, which cause compliance problem in remembering to properly use the medications. In one embodiment, one or more of the above mentioned medications can be included in the polymeric slow release absorbable implants. As one example, the implant may contain prostaglandin analogs and release medication at a constant rate of 10 µg/day-50 µg/day, thereby providing the medication for six months to a few years. As one example, the implant may contain beta-blockers for a patient being treated for a cardiovascular problem, and the implant may release medication at a constant rate of 10 µg/day-50 µg/day, thereby providing the medication for six months to a few years. As one example, the implant may contain ROCK inhibitor and release medication at a constant rate of 10 µg/day-50 µg/day, thereby providing the medication for six months to a few years. As one example, the implant may contain ROCK inhibitor and prostaglandin analogs and release medication at a constant rate of 10 µg/day-50 µg/day, thereby providing the medication for six months to a few years. As one example, the implant may contain an adrenergic agonist, and the implant may release medication at a constant rate of 10 µg/day-50 µg/day, thereby providing the medication for six months to a few years. As one example, the implant may contain a carbonic anhydrase inhibitor, and the implant may release medication at a constant rate of 10 µg/day-50 µg/day, thereby providing the medication for six months to a few years. As one example, the implant may contain a combination of two or more of the above mentioned medications. In one embodiment, the implant may contain a combination of adrenergic agonists and the implant may release the medication at a constant rate of 10 µg/day-50 µg/day, thereby providing the medication for six months to a few years. In one embodiment, a plurality of implants can deliver each medication separately. If a patient does not tolerate one medication, that implant may be removed and replaced with an implant containing another medication. The patient could receive the medication by eye drop for a trial period to determine patient tolerance and lack of side effects, prior to implantation of the medication-releasing device. If needed, the implant can be removed and/or replaced with the desired medication(s). In one embodiment, the implant may contain any of briminodine, alpha-2-adrenegic medication, and/or memantine if the patient has not shown any side effect by topical application. In one embodiment the ROCK inhibitor carrier is a nanoparticle such as dendrimer conjugated with the medication and coated with CCP or ACCP, permitting penetration of the ROCK inhibitor both to the anterior and posterior segments of the eye. In one embodiment, the implant carries derivatives of cannabinoid receptors that affect aqueous humor dynamics.

In one embodiment, the implant is placed in the subconjunctival space anterior or posterior to the insertion of the eye muscles as a long string to release the medication through the sclera. A small space is surgically created under the conjunctiva, specifically, a curved spatula is inserted through a small incision made in the conjunctiva and travels 180 degrees around the sclera from the upper side and retrieving it through the same incision through the same conjunctival incision in the lower side. The string-like implant is placed in this space, providing extended drug delivery. In one embodiment the implant is implanted under the tenon capsule. In one embodiment the implant is placed inside the choroid. In one embodiment the implant is located inside the eye. In one embodiment, the polymeric material is used as a flat semilunar structure as an implant or placed under the inferior conjunctiva. A semicircular or circular polymer band, or explant, has the thickness or length of the disclosed implant implanted in the suprachoroidal space, under the sclera. The same implant can be placed over the sclera under the conjunctiva, i.e., an explant, instead of inside the sclera. Thus, in one embodiment, the ROCK inhibitor is released by placing a semilunar flat absorbable polymeric explant in the inferior part of the limbus so that the inferior part of the explant reaches the inferior cul de sac of the conjunctiva.

Glaucoma is also considered a neurodegenerative disease. Glaucoma thus can affect survival of the retinal ganglion cells (RGC) and their nerve fiber layer (NFL) if intraocular pressure is not adequately controlled. This precaution encompasses patients having open angle glaucoma, and includes patients with low tension glaucoma and/or patients suffering from an optic nerve disorder. Some studies have shown that alpha-2-adrenergic agents, brimonidine, memantine, an NMDA open-channel receptor antagonist, or nerve growth factor (NGF) are neuroprotective. This effect includes upregulation of the brain-derived neurotrophic factors or other agents protecting the RGC in glaucoma.

In one embodiment, the therapeutic approach to replace the ganglion cells and nerve fiber layer involves the use of ROCK inhibitors with or without simultaneous stem cell therapy. Stem cells may be embryonic stem cells, mesenchymal stem cells, or neuronal stem cells. The stem cells are grown in vitro with or without modification of their genetic components using a CRISPR-cas system. The stem cells and ROCK inhibitors may be administered together in an implant, e.g., a tube-shaped implant, as previously described, or injected in the vitreous cavity, or intra- or subretinally.

The agents may be in any biocompatible formation as known to one skilled in the art. The agents may be formulated as microspheres, microcapsules, liposomes, nanospheres, nanoparticles, etc. as known to one skilled in the art.

The general configuration of the device 29 is new. The device is implanted by any of three different methods in various parts of the eye. In one method, the device is configured for implanting over the lens capsule and between the iris 25 and the lens 15 in the posterior chamber. In one method, the device 29 is configured for implanting in the suprachoroidal space; in this embodiment, agent contained in and/or on or with the device is delivered to the choroid 26 and retina 28. In one method, the device 29 is configured for implanting in the subretinal space; in this embodiment, agent contained in and/or on or with the device is delivered to the sensory retina.

In an intralens device, the device 29 may be of any shape. The following embodiments are illustrative only and are not limiting. In one embodiment, the device is ring shaped 29e, 29j. In one embodiment, the device is shaped as an open ring 29e (e.g., doughnut or tire shape). In one embodiment, the device is shaped as a rod 29a, 29b, which may be straight or curved 29c, 29d. In one embodiment, the device 29 is shaped as a semicircle 29c. In one embodiment, the device 29 contains one ring 29e. In one embodiment, the device contains at least two concentric rings 29j. In one embodiment, the device 29 is shaped as an oval 29k. In one embodiment, the device 29 is C shaped 29d. In one embodiment, the device 29 is shaped as triangle 29h. In one embodiment, the device 29 is shaped as a quadratic 29i. In one embodiment, the device 29 is spring-shaped 29g. In one embodiment, the device 29 is shaped in a zigzag configuration 29f. A tube structure permits delivery of agent that must be in a liquid medium, such agents include agents for gene modification or stem cells.

In one embodiment, the size of the device 29 ranges from 1 mm in diameter up to about 34 mm in diameter. In one embodiment, the size of the device 29 ranges from 1 mm in diameter up to about 20 mm in diameter. In one embodiment, the thickness of the device 29 may range from about 50 µm to about 3000 µm. In one embodiment, the thickness of the device 29 may range from about 10 µm to about 3000 µm. In one embodiment, the device 29 is made from a polymeric material that is absorbable. In one embodiment, the device 29 is made from a polymeric material that is nonabsorbable, e.g., polylactic acid polyglycolic acid, silicone, acrylic, polycaprolactone, etc. In one embodiment, the device 29 is made as microspheres.

The device 29 is positioned in the lens capsule, e.g., after cataract extraction prior to or after IOL implantation. In one embodiment, it is positioned inside the lens capsule after cataract extraction and acts as a polymeric capsular expander keeping the capsular bag open for intraocular lens (IOL) implantation). In one embodiment, the device 29 is positioned on the haptics of the IOL. In one embodiment, the device 29 is located inside the capsule or under the iris supported by the lens zonules, or it can be sufficiently large to lie in the ciliary sulcus, or ciliary body, or hanging from the zonules in a C-shaped configuration.

For implantation, after removing the lens cortex and nucleus inside the capsule through a capsulotomy, the inventive device 29 is implanted before or after an IOL is implanted. The inventive device 29 is flexible, deformable, and re-moldable. In one embodiment, the inventive device 29 is implanted through a incision one mm or less using an injector, forceps, etc. The incision may be made in the cornea for cataract removal. In one embodiment, the inventive device 29 is implanted in an eye without cataract extraction. In this embodiment the inventive device 29 may be implanted under the iris, e.g., after traumatic anterior segment injury, and lies over the crystalline lens, IOL, and zonules. Implantation may be facilitated by using a viscoelastic material such as healon, methyl cellulose, etc.

Retino-choroidal diseases are aggravated after cataract surgery. Retino-choroidal diseases include, but are not limited to, diabetes, existing prior inflammations such as uveitis, vascular occlusion, wet age related macular degeneration, etc. Patients with these diseases are candidates for the inventive drug delivery system and method. Other indications are prophylactic therapy prior to development of retinal complications, such as inflammation (CME) and infection, and therapy for an existing disease. Other indications are conditions in which any intraocular drug delivery to treat aging processes if cataract surgery is contemplated or after IOL implantation. In latter situation, the inventive device can be implanted in the capsule or over the IOL under the iris Other indications are post-surgical inflammations, post-surgical infections such as after cataract extraction, and any intraocular delivery.

In one embodiment, medication can be coated on a surface and eluted from the surface of the inventive device for delivery, using methods known in the art (e.g., drug-coated stents). In one embodiment, medication can be incorporated in the polymeric material using methods known to one skilled in the art. The following medications can be delivered, alone or in combinations, to treat eyes using the inventive system and method: steroids, non-steroidal anti-inflammatory drugs (NSAIDS), antibiotics, anti-fungals, antioxidants, macrolides including but not limited to cyclosporine, tacrolimis, rapamycin, mycophenolic acid and their analogs, etc. For example, voclosporin (FIG.) is a next generation calcineurin inhibitor, an immunosuppressive compound, developed for the treatment of uveitis, an inflammation of the uvea, the treatment of psoriasis, and for the prevention of organ rejection in renal transplant patients. It can be used with other immunomodulatores, etanercept, infliximab, adalimumab, etc. Other examples include: antibodies (e.g., anti-vascular endothelial growth factor), immunomodulators, antiproliferative agents, gene delivery agents (e.g., to treat damaged neuronal tissue), neuroprotective agents, anti-glaucoma agents (e.g., to treat or prevent increases in intraocular pressure, etc.). In one embodiment, combinations of agents may be provided in a single device or in multiple devices.

The duration of delivery is manipulated so that the agent(s) is released at a quantity needed to achieve therapeutic effect for each agent, if more than one agent is administered, as long as necessary. Duration may be a single dose, may be one day, may be daily for up to 12 months or longer, may be several times a day. In embodiments using a polymer, reimplantation is possible through a small incision once the polymer is absorbed.

Other variations or embodiments will be apparent to a person of ordinary skill in the art from the above description. Thus, the foregoing embodiments are not to be construed as limiting the scope of the claimed invention.

What is claimed is:

1. A method of treatment comprising
   applying laser therapy to the retina of an eye of a patient using laser pulses having a wavelength of 400-1300 nm and a pulse time duration of a femtosecond up to one second without producing a visible burn in the retina of the eye, the laser therapy using a laser spot size of about 20 µm to 1 mm, and the laser therapy producing an inflammatory response that induces localized release factors for attracting cells to remove tissue debris and inducing repair in the retina of the eye; and
   providing a ROCK inhibitor to treat at least one of an ocular or neurodegenerative disorder using a porous tubular polymer implant device, the device placed by implanting in the eye of the patient in need of treatment, the device 1 mm to 60 mm in length; deformable; containing a ROCK inhibitor in a preparation that includes nanoparticles or microparticles being used as carriers of the ROCK inhibitor, and with a cell penetrating peptide to extend the preparation penetration to the posterior segment of the eye, the anterior segment of the eye, or from the cornea to the retina; shaped to stably fit in the eye and positioned inside the lens capsule of the eye, to provide a relatively longer duration of ROCK inhibitor release over a relatively larger space-occupying area inside the eye so as to inhibit an inflammatory process resulting from the ocular or neurodegenerative disorder, where the ocular or neurodegenerative disorder is selected from the group consisting of age-related macular degeneration wet form, age-related macular degeneration dry form, diabetic retinopathy, retinitis pigmentosa, macular edema, optic nerve disorder, and combinations thereof;

wherein the device is implanted inside the lens capsule of the eye after cataract extraction and acts as a polymeric capsular expander keeping the lens capsule open for intraocular lens implantation.

2. The method of claim 1 where the device releases the ROCK inhibitor for 1 year-3 years at a rate of about 1 µg/day-5 µg/day.

3. The method of claim 1 where the ROCK inhibitor is selected from the group consisting of Fasudil, Ripasudil, RKI-1447, Y-27632, GSK429286A, Y-30141, and combinations thereof.

4. The method of claim 1 where the implant device is biodegradable or non-biodegradable.

5. The method of claim 1 where the device containing the ROCK inhibitor also contains at least one of an anti-platelet derived growth factor (PDGF), an integrin inhibitor, a beta-blocker, an adrenergic agonist, a carbonic anhydrase inhibitor, a cholinergic agent, a prostaglandin analog, a derivative of cannabinoid receptors, and combinations thereof.

6. The method of claim 1 where agent release ranges from 1 month up to 2 years at a rate of 1 µg/day-5 µg/day.

7. The method of claim 1 where the device containing the ROCK inhibitor also contains an anti-vascular endothelial growth factor (anti-VEGF) agent.

8. The method of claim 1 wherein the localized release factors induced by the inflammatory response to the laser therapy further attracts endogenous stem cells and/or stem cells administered to the eye of the patient so as to treat cell loss in the eye of the patient.

9. The method of claim 1 where the preparation includes nanoparticles, and the nanoparticles are coated with an antibody against a protein present in a neurodegenerative disease.

10. The method of claim 1 where the preparation includes nanoparticles, and the nanoparticles are sized to pass through the intercellular space of the retina of the eye and accumulate under the retina, thereby being effective both for retinal and choroidal disease processes affecting each of the retina and choroid.

11. The method of claim 10 where the nanoparticles are selected from the group consisting of dendrimers, aptamers, micelles, and combinations thereof.

12. The method of claim 10 where the nanoparticles are in the form of dendrimers.

13. The method of claim 1 where the preparation is a mucophilic preparation comprising chitosan or hyaluronic acid.

14. The method of claim 1 where the device containing the ROCK inhibitor also contains a medication selected from the group consisting of an anti-vascular endothelial growth factor (anti-VEGF) agent, a macrolide, a calcineurin inhibitor, and combinations thereof.

* * * * *